Reissued Jan. 31, 1928. Re. 16,866

UNITED STATES PATENT OFFICE.

RUSSELL B. CROWELL, OF AGNEW, AND GERALD F. BRECKENRIDGE, OF SAN JOSE, CALIFORNIA, ASSIGNORS, BY MESNE ASSIGNMENTS, TO AMERICAN SOLVENTS & CHEMICAL CORPORATION OF CALIFORNIA, A CORPORATION OF DELAWARE.

PROCESS FOR PRODUCING ALKALI-METAL XANTHATES.

No Drawing. Original No. 1,559,504, dated October 27, 1925, Serial No. 31,203, filed May 18, 1925. Application for reissue filed December 22, 1927. Serial No. 242,004.

This invention relates to processes of producing salts of xanthic or ethyloxydithiocarbonic acid of the alkali metals such as sodium or potassium.

It has been proposed to produce the alkali metal xanthates such as sodium or potassium xanthates by causing a reaction to take place between a hydroxide of the alkali metals such as sodium or potassium, carbon bisulphide, and ethyl alcohol, the reaction being carried out either in the presence of an aqueous medium or in the presence of an excess of alcohol. In processes wherein this reaction is carried out in an aqueous medium the water has the effect of materially reducing the percentage yield of the xanthate salts thereby causing an increase in the cost thereof. Processes in which the reaction takes place in the presence of an excess of alcohol present the disadvantage that the alcohol utilized in the process is either lost or is recovered only with great difficulty therefrom, thereby causing such processes to be necessarily costly. Another well known process of producing sodium xanthate is that in which the metal sodium is dissolved in dry alcohol, and to this solution is added a calculated quantity of dry carbon bisulphide, the reacting mixture being continuously cooled and agitated until the reaction is complete.

Accordingly, one of the objects of this invention is to provide an improved process of producing alkali metal xanthates wherein a mixture of a hydroxide of an alkali metal, carbon bisulphide, and alcohol are reacted in the absence of either an aqueous medium or an excess of alcohol.

Another object of this invention is to provide an improved method of producing the salts of xanthic acid of the alkali metals which results in a high percentage yield of such salts in a substantially purer state and at lower cost than is the case in the processes of the prior art.

Other and further objects of this invention will appear from the more detailed description of this invention set forth hereinafter, it being understood that various changes may be made therein by those skilled in the art without departing from the scope and spirit of this invention as defined in the appended claims.

In one preferred embodiment of carrying out our invention we take either anhydrous sodium or potassium hydroxide, the choice of the hydroxide being dependent upon which one of the particular xanthate salts of the alkali metals, is desired, in amounts equivalent to their molecular weights and grind or reduce the same to a granular or powdered state with the particles of such size that the crushed material will pass through a screen of 80 mesh or greater. This pulverulent anhydrous material is then admixed with a hydrocarbon liquid body as kerosene, gasolene, toluene, or a similar liquid which possesses the inherent property of being chemically inert to such hydroxides, under vigorous agitation. As soon as the hydroxide is thoroughly disseminated throughout the body of hydrocarbon liquid and while the hydroxide hydrocarbon mixture is being vigorously agitated, ethyl alcohol or commercial alcohol in an amount corresponding to its molecular weight is added thereto. Upon contact of the alcohol with hydroxide hydrocarbon mixture, heat is evolved and a semi-colloidal suspensoid having the appearance of a gel-like precipitate is formed. To this suspensoid mixture is then added gradually and slowly, carbon bi-sulphide in amount equivalent to its molecular weight. While the carbon bisulphide is being added to the mixture containing the suspensoid, the reacting mass is cooled and simultaneously subjected to vigorous agitation, such agitation and cooling being continued until the reaction is complete. The xanthate salt, either the sodium or potassium xanthate dependent upon the specific hydroxide compound utilized in the process appears as a yellow precipitate, and can be readily recovered from the mass.

The procedure outlined above may be varied in that the finely ground anhydrous hydroxide of sodium or potassium in an amount equivalent to its molecular weight may be added to the kerosene, gasolene or similar liquids, the mixture then vigorously stirred until a suspensoid of the hydroxide in a liquid non-aqueous medium is produced, and then adding to the suspensoid mass a mixture consisting of alcohol and carbon bisulphide in amounts equivalent to their molecular weights, the whole mass being vigorously agitated and cooled during the reaction. The procedure may be further modified by adding a part of the requisite amount of alcohol to the hydroxide suspensoid mixture, and a part of the alcohol to the requisite amount of carbon bisulphide, and then bringing the two portions together, under vigorous agitation in a vessel provided with suitable cooling means through which an appropriate cooling medium is caused to circulate, during the interval in which the mass reacts and the reaction is completed.

The percentage yield of the xanthate salts of the alkali metals as sodium or potassium produced by the processes hereinabove set forth is high, and such salts are in a substantially pure state. The xanthate salts may be readily recovered from the reacted mass and may be dried in the usual manner or if desired for immediate use may be dissolved in water.

Having described our invention, what we claim as new and desire to secure by Letters Patent is:

1. The process of producing alkali metal xanthates which comprises reacting a suspended hydroxide of an alkali-metal, alcohol, and carbon bisulphide in a liquid hydrocarbon medium chemically inert to the remaining ingredients.

2. The process of producing alkali-metal xanthates which comprises reacting a mixture of a suspended hydroxide of an alkali-metal, alcohol, and carbon bisulphide, in a liquid hydrocarbon medium chemically inert to the remaining ingredients, said mixture being subjected to agitation and being cooled during the reaction.

3. In the process of producing alkali-metal xanthates the steps which comprise forming a suspension of an anhydrous alkali-metal hydroxide in a liquid hydrocarbon medium chemically inert to said hydroxide, and adding alcohol thereto.

4. In the process of producing alkali-metal xanthates the steps which comprise forming a suspension of an alkali-metal hydroxide in a liquid hydrocarbon medium chemically inert to said hydroxide and adding alcohol and carbon bisulphide thereto.

5. In the process of producing alkali-metal xanthates the steps which comprise forming a suspension of anhydrous alkali-metal hydroxide in a liquid hydrocarbon medium chemically inert to the said hydroxide, adding alcohol thereto, and then adding carbon bisulphide.

6. The process of producing alkali metal xanthates which comprises forming a suspension of an alkali metal hydroxide in a liquid hydrocarbon chemically inert to said hydroxide, adding alcohol thereto, and then adding a mixture of alcohol and carbon bisulphide to the alcohol hydroxide mixture.

7. The process as set forth in claim 6 wherein the hydroxide suspension is subjected to agitation during the addition of the alcohol thereto.

8. The process as set forth in claim 6 wherein the alcohol hydroxide mixture is cooled and vigorously agitated during the addition of the mixture of alcohol and carbon bisulphide thereto.

9. The process of producing alkali metal xanthates which comprises forming a suspension of an alkali metal hydroxide in a liquid hydrocarbon chemically inert to said hydroxide, adding alcohol thereto, cooling the mixture, adding carbon bisulphide, and recovering the salt thus produced.

10. The process of producing alkali metal xanthates which consists in forming a suspension of an alkali metal hydroxide in a liquid hydrocarbon chemically inert to said hydroxide, adding alcohol thereto, cooling the mixture, adding an admixture of alcohol and carbon bisulphide to said mixture, and recovering the salts thus produced.

In testimony whereof we affix our signatures.

RUSSELL B. CROWELL.
GERALD F. BRECKENRIDGE.